United States Patent [19]

Takemura et al.

[11] Patent Number: 5,583,218

[45] Date of Patent: Dec. 10, 1996

[54] CARBAPENEM DERIVATIVES

[75] Inventors: Makoto Takemura; Toshiyuki Nishi; Hiroshi Susaki; Youhei Ishida; Hiroko Koda; Takeshi Hayano, all of Tokyo, Japan

[73] Assignee: Daiichi Pharmaceutical Co., Ltd., Tokyo, Japan

[21] Appl. No.: 601,142

[22] Filed: Feb. 13, 1996

Related U.S. Application Data

[63] Continuation of Ser. No. 437,073, May 5, 1995, abandoned, which is a continuation of Ser. No. 2,680, Jan. 8, 1993, abandoned, which is a continuation of Ser. No. 433,303, Nov. 8, 1989, abandoned.

[30] Foreign Application Priority Data

Nov. 8, 1988 [JP] Japan .................... 63-281798

[51] Int. Cl.$^6$ .................... C07D 487/01
[52] U.S. Cl. .................... 540/350
[58] Field of Search .................... 514/350

[56] References Cited

FOREIGN PATENT DOCUMENTS

| | | |
|---|---|---|
| 0050334 | 10/1981 | European Pat. Off. . |
| 0071908 | 7/1982 | European Pat. Off. . |
| 0168707 | 7/1985 | European Pat. Off. . |
| 0169410 | 7/1985 | European Pat. Off. . |
| 2263-04 | 6/1987 | European Pat. Off. ........ 540/350 |
| 0289801 | 4/1988 | European Pat. Off. . |

OTHER PUBLICATIONS

Chemical Abstracts, vol. 107, No. 19, Nov. 9, 1987, p. 697, Abstract No. 175781k, Columbus, Ohio, US.

*Primary Examiner*—Robert Gerstl
*Attorney, Agent, or Firm*—Sughrue, Mion, Zinn, Macpeak & Seas

[57] ABSTRACT

Carbapenem derivatives of formula (I):

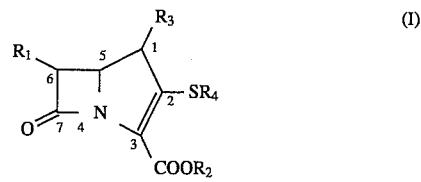

wherein (a) $R_1$ is a hydrogen atom, an alkyl group of from 1 to 6 carbon atoms, a hydroxy-lower alkyl group or a protected hydroxy-lower alkyl group of from 1 to 6 carbon atoms in its alkyl moiety, (b) $COOR_2$ is a carboxyl group, a carboxylate anion or a protected carboxyl group, (c) $R_3$ is an alkyl group of from 1 to 6 carbon atoms and (d) $R_4$ is a substituted or unsubstituted heterobicyclic group of formula (II):

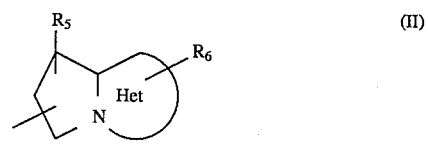

in which the partial structure

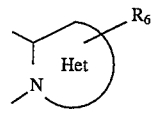

is a 5- or 6-membered, saturated or unsaturated, nitrogen-containing heterocycle containing 1 to 4 hereto atoms each selected from the group consisting of oxygen, sulfur and nitrogen, at least one hetero atom being nitrogen, and is which $R_5$ and $R_6$ each is a hydrogen atom or an appropriate substituent, any isomeric form thereof, and pharmacologically acceptable salts thereof are potent and stable antimicrobial agents.

13 Claims, No Drawings

CARBAPENEM DERIVATIVES

This is a continuation of Application Ser. No. 08/437,073, filed May 5, 1995, which is a continuation of Ser. No. 08/002,680 filed Jan. 8, 1993, which is a continuation of Ser. No. 07/433,303 filed Nov. 8, 1989 all are now abandoned.

FIELD OF THE INVENTION

This invention relates to carbapenem derivatives having a bicyclic heterocycle-thio group at position 2 and an alkyl group at position 1 and to salts thereof.

BACKGROUND OF THE INVENTION

A variety of potent, broad-spectrum penicillins and cepharosporins are known and have been used as antibiotics for therapeutic purposes. They are very effective in treating various infectious diseases. In the medical field, effective antimicrobial agents have been put to practical use one after another and, accordingly, pathogenic bacteria have acquired resistance thereto following introduction of each antimicrobial agent. Such a situation always requires a further new antimicrobial agent. Such is also the case with the above-mentioned penicillins and cepharosporins and, as a result of the development of resistance thereto in bacteria, the penicillins and cepharosporins currently in use are already not always wholly satisfactory from the standpoint of antimicrobial activity, pharmacokinetics and/or safety.

Thienamycin is one of known carbapenems (JP-A-51-73191) (the term "JP-A" as used herein means an "unexamined published Japanese patent application"), and U.S. Pat. No. 3,950,357. It is effective even against bacteria resistant to penicillin and cepharosporin antibiotics and thus has a broad antibacterial spectrum. Therefore, since the discovery of thienamycin, efforts have been made to synthesize carbapenem derivatives and compounds having skeletons similar to thienamycin. However, so-far the known carbapenem and penem antibiotics are physico-chemically unstable and are readily degradable upon exposure to kidney dehydropeptidase, among other enzymes; no compounds have been identified as being useful as drugs.

As mentioned above, while antibiotics are effective in the treatment of infectious diseases, there is the problem of development of resistance in bacteria. Those penicillin and cepharosporin antibiotics which have been used universally because of their having a broad antibacterial spectrum are no exception and, as resistance thereto develops in bacteria, they become targets of criticism from the standpoint of their antibacterial spectrum among other characteristics.

SUMMARY OF THE INVENTION

Accordingly, it is an object of the invention to provide novel antibiotics which have a broad antibacterial spectrum, are effective also against bacterial strains resistant to penicillin and cepharosporin antibiotics and have favorable physico-chemical properties.

As a result of the intensive investigations, the present inventors found that novel carbapenem derivatives having the general formula (I) given below have a very broad antibacterial spectrum, showing potent antibacterial activity against gram-positive and gram-negative bacteria as well as against obligate anaerobes, even against bacterial strains resistant to penicillins and cepharosporins. It has been also found that the carbapenem derivatives have good physico-chemical stability and are resistant to enzymatic degradation by kidney dehydropeptidase I, beta-lactamase and the like and, therefore, are highly valuable as drugs. The present invention has been completed based on these findings.

The invention thus provides carbapenem derivatives of formula (I):

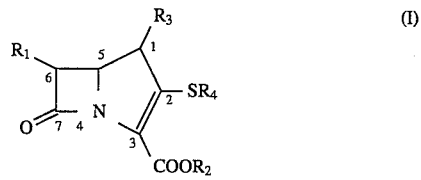

any isomeric form thereof and pharmacologically acceptable salts thereof.

In the above formula, (a) $R_1$ is a hydrogen atom, an alkyl group of from 1 to 6 carbon atoms, a hydroxy-lower alkyl group or a protected hydroxy-lower alkyl group of from 1 to 6 carbon atoms in its alkyl moiety;

(b) $COOR_2$ is a carboxyl group, a carboxylate anion or a protected carboxyl group;

(c) $R_3$ is an alkyl group of from 1 to 6 carbon atoms; and (d) $R_4$ is a substituted or unsubstituted heterobicyclic group of formula (II):

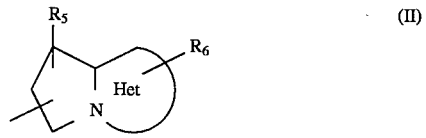

in which the partial structure

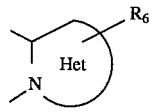

is a 5- or 6-membered, saturated or unsaturated, nitrogen-containing heterocycle containing 1 to 4 hetero atoms each selected from the group consisting of oxygen, sulfur and nitrogen, at least one hetero atom being nitrogen, and is which $R_5$ and $R_6$ are the same or different and each is selected from the group consisting of a hydrogen atom, a halogen atom, a hydroxyl group, a carbamate group, an alkoxy group of from 1 to 6 carbon atoms, an amino group, an acylamino group, a ureido group, an alkylthio group of from 1 to 6 carbon atoms, a sulfenyl group, a sulfinyl group, a sulfonamido group, a carbamoyl group, a cyano group, a nitro group, an amidino group, a quanidino group, a hydroxycarbamoyl group, a thiocarbamoyl group, a trifluoromethyl group, an imino group, a $C_1$–$C_6$ alkyl group which may be substituted, a $C_2$–$C_6$ alkenyl group which may be substituted, a $C_2$–$C_6$ alkynyl group which may be substituted, a $C_3$–$C_6$ cycloalkyl group which may be substituted, a $C_3$–$C_6$ cycloalkenyl group which may be substituted, a heterocyclyl group which may be substituted, a heterocyclyl-$C_1$–$C_6$ alkyl group which may be substituted, a heterocyclyl-$C_2$–$C_6$ alkenyl group which may be substituted, a heterocyclyl-$C_2$–$C_6$ alkynyl group which may be substituted, a $C_3$–$C_6$ cycloalkylidene group which may be substituted, a $C_3$–$C_6$ heterocyclylidene group which may be substituted, and an aryl group which may be substituted, the substituent or substituents on the group $R_5$ or $R_6$ being selected each independently from the group consisting of a halogen atom, a hydroxyl group, an alkoxy group of from 1 to 6 carbon atoms, a carbamoyloxy group which may have one or two substituents selected from the group consisting of a $C_1$–$C_6$ alkyl group, an aryl group and a heteroaryl group on the nitrogen atom, an amino group which may have one or two substituents selected from the group consisting of a $C_1$–$C_6$ alkyl group, an aryl group and a heteroaryl group on the nitrogen atom, an alkylammonio group which may have up to three $C_1$–$C_6$ alkyl groups, an acylamino group which may have a substituent selected from the group consisting of a $C_1$–$C_6$ alkyl group, an aryl group and a heteroaryl group on the nitrogen atom, a formylamino group, a ureido group which may have 1 to 4 substituents selected from the group consisting of $C_1$–$C_6$ alkyl group, an aryl group and a heteroaryl group on either or both of the nitrogen atoms, an alkylthio group, a sulfenyl group, a sulfinyl group, a sulfamoyl group which may have one or two substituents selected from the group consisting of a $C_1$–$C_6$ alkyl group, an aryl group and a heteroaryl group on the nitrogen atom, a sulfinamoyl group which may have one or two substituents selected from the group consisting of a $C_1$–$C_6$ alkyl group, an aryl group and a heteroaryl group on the nitrogen atom, a carbamoyl group which may have one or two substituents selected from the group consisting of a $C_1$–$C_6$ alkyl group, an aryl group and a heteroaryl group on the nitrogen atom, a cyano group, a nitro group, an amidino group which may have one or two substituents selected from the group consisting of a $C_1$–$C_6$ alkyl group, an aryl group and a heteroaryl group on either or both of the nitrogen atoms, a guanidino group which may have one or two substituents selected from the group consisting of a $C_1$–$C_6$ alkyl group, an aryl group and a heteroaryl group on one or two of the nitrogen atoms, a hydroxycarbamoyl group which may have a substituent selected from the group consisting of a $C_1$–$C_6$ alkyl group, an aryl group and a heteroaryl group on the nitrogen atom thereof, a thiocarbamoyl group which may have one or two substituents selected from the group consisting of a $C_1$–$C_6$ alkyl group, an aryl group or a heteroaryl group on the nitrogen atom, a trifluoromethyl group, an alkoxyimino group, a $C_1$–$C_6$ alkoxycarbonyl group which may be substituted, and a $C_1$–$C_6$ alkylcarbonyloxy group which may be substituted.

Among the carbapenem derivatives of the general formula (I), the following compounds (Ia) to (If) are preferred.

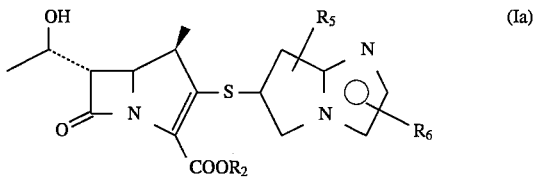
(Ia)

wherein $R_2$ is a hydrogen atom or $COOR_2$ is a carboxylate anion and $R_5$ and $R_6$ are the same or different and each is a hydrogen atom, —$CH_3$, —$CH_2OH$, —$CONH_2$, —$CONHCH_3$ or —$CON(CH_3)_2$,

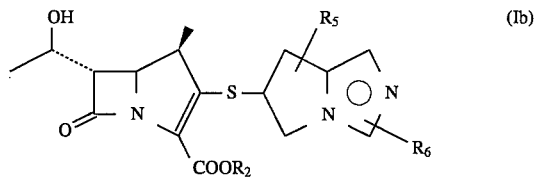
(Ib)

wherein $R_2$ $R_5$ and $R_6$ are as defined in the above formula (Ia),

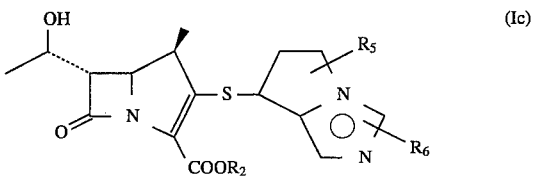
(Ic)

wherein $R_2$ $R_5$ and $R_6$ are as defined in the above formula (Ia),

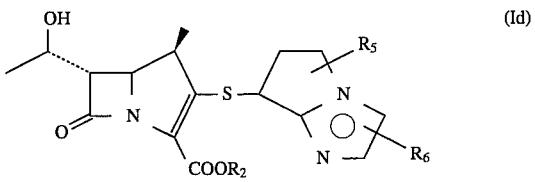
(Id)

wherein $R_2$ $R_5$ and $R_6$ are as defined in the above formula (Ia),

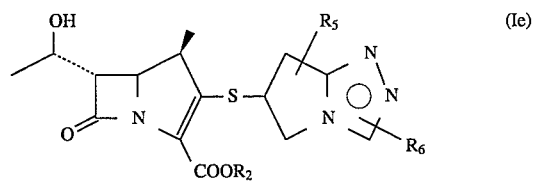
(Ie)

wherein $R_2$ $R_5$ and $R_6$ are as defined in the above formula (Ia),

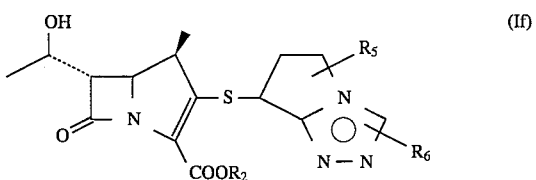
(If)

wherein $R_2$ $R_5$ and $R_6$ are as defined in the above formula (Ia).

Referring to the above general formula (I), the substituents $R_1$, $R_2$, $R_3$ and $R_4$ in preferred carbapenem derivatives are as follows.

$R_1$ is preferably a hydrogen atom or a $C_1$–$C_6$ alkyl group (e.g. methyl, ethyl, n-propyl, isopropyl, n-butyl), which may optionally have a hydroxyl group. And further, said hydroxyl group may be protected by a known protective groups, e.g., an alkoxycarbonyl group such as methoxy carbonyl group, ethoxycarbonyl group, propyloxycarbonyl group, and t-butyloxycarbonyl group; a halogenoalkoxycarbonyl group such as 2-iodoethyloxycarbonyl group and 2,2,2-trichloroethyloxycarbonyl group; an aralkyloxycarbonyl group such as benzyloxycarbonyl group, o-nitrobenzyloxycarbonyl group, p-nitrobenzyloxycarbonyl group, and p-methoxybenzyloxycarbonyl group; a substituted silyl group such as trimethylsilyl group, t-butyldimethylsilyl group, and t-butyldiphenylsilyl group; a substituted methyl group such as methoxymethyl group, 2-methoxyethoxymethyl group, and methylthiomethyl group; a cyclic ether such as tetrahydropyranyl group and tetrahydrofuranyl group; an alkyl group such as allyl group and t-butyl group.

$R_2$ is preferably a hydrogen atom, a straight or branched $C_1$–$C_4$ alkyl group (e.g., methyl, ethyl, isobutyl, tert-butyl), a $C_1$–$C_6$ alkoxy-$C_1$–$C_6$ alkyl group (e.g., methoxymethyl, methoxyethyl), a $C_1$–$C_6$ aliphatic acyloxymethyl group (e.g., pivaloyloxymethyl), a phthalidyl group, or an ester residue which serves also as a carboxy-protecting group in the production of the compounds according to the invention and which is readily eliminable under mild conditions, for example, an aralkyl group (e.g., o-nitrobenzyl, p-nitrobenzyl, benzhydryl, 2-naphthylmethyl), an aryl group or a $C_1$-$C_6$ alkylsilyl group (e.g., trimethylsilyl).

$COOR_2$ may be a carboxylate anion. This means that the carboxyl group at position 3 of the carbapenem skeleton of a compound according to the invention takes the form of a carboxylate anion serving as a counter ion to the substituent $R_4$ depending on the state of said substituent. For example, when $R_4$ is a quaternary nitrogen-containing heterocyclic group, $COOR_2$ occurs as a carboxylate anion, serving as a counter ion to the quaternary nitrogen. When a compound according to the invention is in the form of a salt with a strong acid or, in other words, when an anion derived from said strong acid serves as a counter ion to the quaternized nitrogen, $R_2$ may be a hydrogen atom. In such a case, the compound has properties characteristic of the so-called betaine compounds and such acid addition salt form of the compound of general formula (I) may be represented by the following formula:

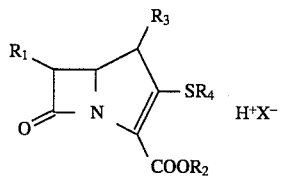

wherein $X^-$ is an acid-derived anion. Furthermore, when $R_4$ is a basic group, $COOR_2$ occurs either as a carboxyl group or as a carboxylate anion depending on the environment (pH) in which the compound according to the invention is placed. This means that $COOR_2$ has the so-called zwitter ion structure typical of amino acids. It is to be noted that compounds having such zwitter ion structure also fall within the scope of the compounds of general formula (I).

$R_3$ is preferably a straight or branched lower $C_1$-$C_6$ alkyl group (e.g. methyl, ethyl, propyl), a $C_1$-$C_6$ alkoxy-$C_1$-$C_6$ alkyl group (e.g. methoxymethyl, methoxyethyl), an aminomethyl group, an acylaminomethyl group, or the like.

Preferred examples of the substituent $R_4$ which the carbapenem derivatives according to the invention should preferably have are of the general formula:

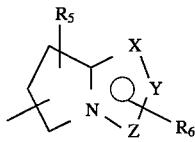

wherein X, Y and Z each is a nitrogen or carbon atom and $R_5$ and $R_6$ are as defined above. More preferably, $R_5$ and $R_6$ each should be selected from the group consisting of:

—H, —OH, —$CH_3$, —$C_2H_5$, —$NH_2$, —$CONH_2$, —$CO_2H$,

—CN, —F, —Cl, —$SCH_3$, —$OCONH_2$, —$OCH_3$,

—$CONHCH_3$, $CONMe_2$, —CON⌒NH, —CON⌒O,

—NHCOCONH2, —SOCH3, —NHCONH2, —N⌒C(=O)NH,

—SO2Me, —SO2NH2, —CSNH2, —NO2, —C(=NH)NH2,

—C(=NMe)NHMe, —C(=NMe)NMe2, —NH—C(=NH)NH2, —CF3,

—C(=N—OH)CH3, —C(=N—OMe)CONH2, —CH2CONH2, —CH2C≡CH,

—CH2CN, —CH2CONHCH3, —CH2CH2OH, —CH2CH2F,

—CH2F, —S-tetrazolyl-Me, —S-(N-Me triazinedione),

—S-(N-Me triazinedione), —N⌒piperidine, —⌒cyclohexyl-NH,

—N⌒NH and —N⌒O.

Thus, the carbapenem derivatives according to the invention preferably have one of the following heterobicyclic groups ($R_4$):

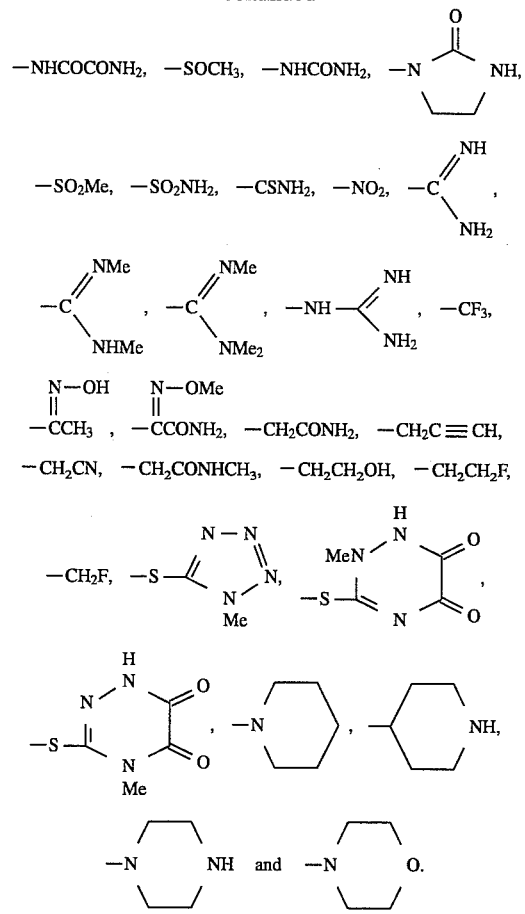

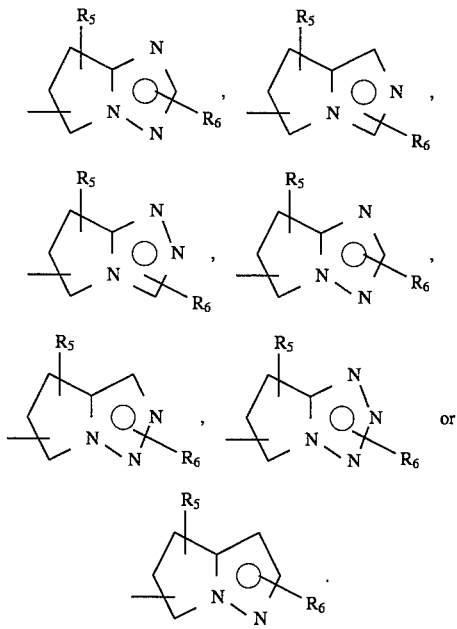

When $R_4$ contains one or more asymmetric carbon atoms, stereoisomerism is encountered. Thus, for instance, when there is one asymmetric carbon atom in $R_4$, two stereoisomers are involved; hereinafter, one of them is referred to as "isomer A" and the other as "isomer B" for convenience sake.

Referring to general formula (I), the carbon atom at position 5 should preferably have the same configuration as is the case with naturally occurring thienamycin; the hydrogen atom attached to said carbon atom lies in an α-configuration. The configuration of said carbon atom is R in the case of thienamycin. However, the configuration of said carbon atom of the compound of the present invention is S, since the compound of the present invention has an alkyl group at position 1. Preferred as $R_1$ are a hydrogen atom and a 1-hydroxyethyl group. In particularly preferred examples, the carbon atom at position 6, with a 1-hydroxyethyl group attached thereto, has an S configuration and the carbon atom at position 8 to which the hydroxyl group is attached has an R configuration. $R_3$ can be an alkyl groups of from 1 to 6 carbon atoms, more preferably a methyl group. The resulting asymmetric carbon atom at position 1 should preferably have an R configuration.

More specifically, particularly preferred species of $R_2$ include a hydrogen atom, an anionic charge and such metabolizable ester residues as pivaloyloxymethyl, phthalidyl and acetoxycarbonyloxymethyl. Preferred examples of the ester residue ($R_2$) to serve as a carboxy-protecting group in the synthesis of the compounds of general formula (I) are p-nitrobenzyl and allyl.

Tauromerism may possibly be found in some of the compounds according to the invention and intermediates therefor. In such cases, the tautomers are represented herein only by one of the possible structural formulas. It is to be noted, however, that this is not meant to restrict the scope of the invention.

The following heterobicyclic groups, which may optionally have one or two substituents ($R_5$, $R_6$), are preferred examples of the group $R_4$:

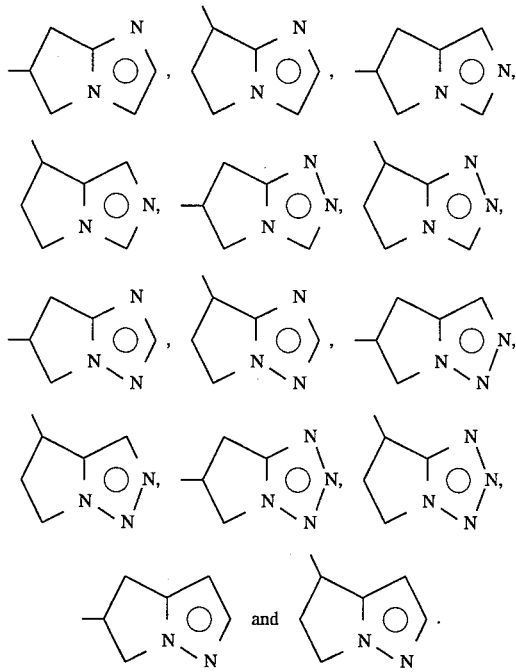

The above-mentioned compounds of general formula (I) may be in the form of pharmacologically acceptable salts, which include, among others, salts with nontoxic carboxylic acids, salts with metals such as sodium, potassium, aluminum and magnesium, and salts with amines such as triethylamine, procaine and benzylamine and with nontoxic amines generally used for salt formation with penicillins and cepharosporins. The sodium salt and potassium salt are particularly preferred, however.

The carbapenem derivatives according to the invention have a basic moiety and therefore can be converted to pharmaceutically acceptable acid addition salts, for example, salts with inorganic acids, such as hydrochloric acid, hydrobromic acid, phosphoric acid and sulfuric acid, or with organic acids, such as acetic acid, citric acid, succinic acid, ascorbic acid and methanesulfonic acid. Particularly preferred are the hydrochloride and sulfate.

The compounds of formula (I) may be solvated with a variety of solvents. Thus, for example, hydrates thereof also fall within the scope of the present invention.

The compounds according to the invention can be admixed with carriers, stabilizers, dissolution aids or solubilizing agents and/or excipients, which are in conventional use, by any of conventional methods to give pharmaceutical preparations.

The preparations may be administered either orally in the form of tablets, pills, capsules, granules and so forth; parenterally in the form of injections for intravenous or intramuscular administrations; as suppositories and so on. Generally, the daily dose for human adults lies within the range of 250 to 3,000 mg and is given in several divided doses. Said dose may suitably be increased or decreased depending on age, sex, symptoms and other factors.

The compounds (I) according to the invention can be produced by the process shown below in terms of reaction formulas:

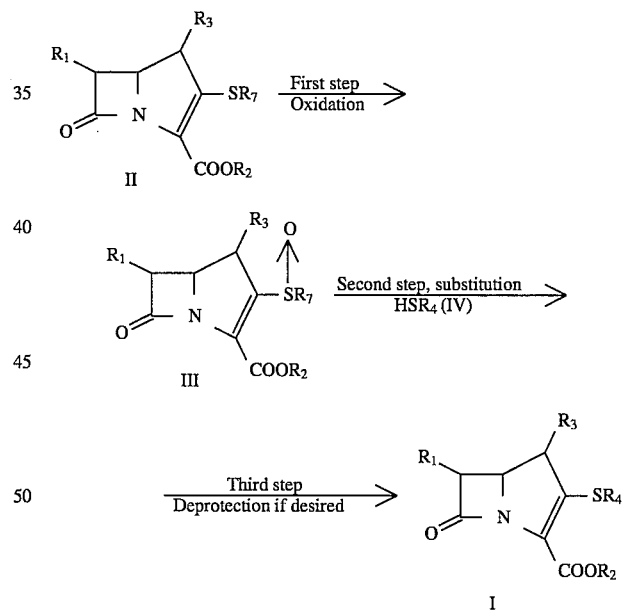

First Step:

A carbapenem derivative of general formula (II) [wherein $R_1$ is as defined above, $R_2$ is the above-mentioned ester residue and $R_7$ is an organic group, for example, an alkyl group (preferably methyl, ethyl, n-propyl, isopropyl), an aryl group (e.g., phenyl, naphthyl), a 2-acylaminoethyl group, a 2-acylaminovinyl group, an aralkyl group (e.g., benzyl methylbenzyl, phenethyl)], which can be synthesized by a known method (JP-A-58-26887 and EP-A-0,071,908) or a modification thereof, is oxidized, in an appropriate solvent, with an oxidizing agent, such as perbenzoic acid, m-chloroperbenzoic acid, peracetic acid, hydrogen peroxide, selenium dioxide, ozone or sodium metaperiodate, preferably m-chloroperbenzoic acid, to give the corresponding sulfoxide (III) in high yield. The sulfoxide thus obtained, though it is a mixture of stereoisomers, can suitably be used in the second step without isomer separation. Solvents suited for use in the first step are halogenated hydrocarbons, such as dichloromethane, chloroform and carbon tetrachloride, alcohols, such as methanol and ethanol, ketones, such as acetone and methyl ethyl ketone, acetic acid, pyridine, N,N-dimethylformamide (hereinafter abbreviated as "DMF"), water, phosphate buffer and other solvents (inclusive of mixed solvents) which will not react with the starting materials or reaction product or otherwise interfere with the reaction. The reaction is advantageously carried out at a temperature of −50° C. to 50° C., preferably under milder temperature conditions (−30° C. to room temperature). A reaction period of 5 minutes to 4 hours, generally 30 minutes to 1 hour, is sufficient for completion of the reaction.

Second Step:

In this step, the sulfoxide (III) obtained in the above manner is subjected to a substitution reaction with the thiol (IV) (EP-A-0,210,883, $R_4$ in the formula being as defined above) or an acid addition salt or a reactive derivative thereof. Solvents suited for use in this step are alcohols, such as methanol and ethanol, ketones, such as acetone and methyl ethyl ketone, DMF, acetamide, dimethyl sulfoxide (DMSO), tetrahydrofuran (THF), acetonitrile, hexamethylphosphotriamide, water and other solvents (inclusive of mixed solvents) which will not react with the starting materials and reaction product or otherwise interfere with the reaction. The reaction is preferably carried out at a temperature of −50° C. to room temperature, more preferably −30° C. to 0° C. for a period of 15 minutes to 2 hours, more preferably 30 minutes to 2 hours.

While the reaction can proceed in the absence of any base, the presence of a base renders the thiol of general formula (IV) more reactive and allows the reaction to proceed more smoothly. Bases suited for use are alkylamines, such as triethylamine and diisopropylethylamine, alicyclic amines, such as 1,8-diazabicyclo-[5,4,0]-7-undecene (hereinafter abbreviated as "DBU") and N-methylmorpholine, inorganic bases, such as sodium hydroxide, potassium hydroxide, potassium carbonate and sodium carbonate, metal alcoholates, such as potassium tert-butoxide and sodium methoxide, sodium amide and so forth. Preferred among them are diisopropylethylamine and DBU.

As examples of the reactive derivative of the thiol compound of general formula (IV), there may be mentioned thiolate compounds of the general formula

MS—$R_4$ wherein M is an alkali metal and $R_4$ is as defined above. In the above-mentioned substitution reaction, the thiol compound of general formula (IV) is used generally in an amount of 1 to 3 equivalents, preferably 1 to 2 equivalents, based on the sulfoxide (III), and the base is preferably used in an amount equivalent to the thiol compound (IV). When the thiol compound (IV) is used in its acid addition salt form, good results can be obtained by adding an additional amount of the base sufficient to neutralize the acid constituting the addition salt.

The substitution product formed by the above reaction can be isolated by an ordinary posttreatment procedure.

Third Step:

When the above-mentioned substitution product has a protective group, the protective group can be eliminated if desired. The deprotection can be effected, for example, by hydrogenation for reductive degradation, by chemical reduction, or by hydrolysis with an acid, base or enzyme.

Where the substituent $R_2$ in general formula (I) is an ester residue such as p-nitrobenzyl, benzhydryl or 2-naphthylmethyl, the deprotection can be effected by catalytic reduction using a known metal catalyst, such as palladium-on-carbon or platinum oxide to give a carbapenem derivative of general formula (I) in which $COOR_2$ is a carboxyl group or a carboxylate anion. Said reduction is carried out in a solvent, such as dioxane, THF, water or a buffer, or a mixed solvent composed of these, preferably hydrous THF, hydrous dioxane or a mixture of a phosphate buffer and THF, at a hydrogen pressure of 1 to 4 atmospheres and at a temperature of 0° C. to 50° C., preferably 10° C. to 30° C., for 30 minutes to 16 hours, preferably 10 minutes to 1 hour, whereby the desired carbapenem derivative of general formula (I) in which $COOR_2$ is a carboxyl group or a carboxylate anion can be obtained. In cases where $R_2$ in general formula (I) is a p-nitrobenzyl group, for instance, reaction with an aqueous solution of ammonium chloride and an iron powder in a water-soluble organic solvent, such as THF or dioxane, can give the desired compound of general formula (I) in which $COOR_2$ is a carboxyl group or a carboxylate anion; in cases where $R_2$ is an allyl group, reaction with tetrakis(triphenylphosphine)palladium(0), triphenylphosphine and 2-ethylhexanoic acid in an aprotic solvent, such as THF or methylene chloride; and in cases where $R_2$ is a 2,2,2-trichloroethyl group, deprotection by zinc powder reduction.

Some of the substitution products from the above-mentioned second step are difficult to isolate and purify because of their physical properties. In such cases, good results may be obtained in producing compounds of general formula (I) in which $COOR_2$ is a carboxyl group or a carboxylate anion when the intermediate substitution products are deprotected in the same reaction vessel or following ordinary simple after-treatment. Such is a simple but excellent means of producing the desired products with good yield and quality, particularly in large amounts, without particular complicacies of operation.

The desired compounds of general formula (I) can be isolated and purified by conventional means, such as extraction and concentration, followed, as necessary, by recrystallization, reprecipitation, chromatography and/or the like. The compounds of general formula (I) can be obtained in high purity by crystallization and, for this purpose, they should preferably be converted to their salt form to give favorable results. In that case, the salt need not always be a nontoxic salt. The desired compounds can be obtained in high purity even from toxic salts by converting them to the free form or to a pharmacologically acceptable salt form after crystallization and purification of said toxic salts.

For producing the compounds of general formula (I) in the form of esters metabolizable in vivo, starting compounds having an appropriate ester-forming group ($R_2$) in their $COOR_2$ group are used or the compounds of general formula (I) in which $COOR_2$ is a carboxyl group or a carboxylate anion are esterified, as is common practice in the field of penicillins and cephalosporins.

The following examples illustrate the process for producing the compounds according to the invention in further detail. It is to be noted, however, that they are by no means limitative of the scope of the invention. The following abbreviations are used herein-after:

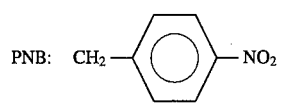

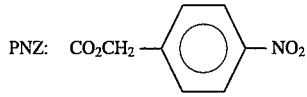

Further, unless otherwise specified, all percents, rates, parts, etc. are by weight.

EXAMPLE 1

Production of (1R,5S,6S,8R)-2-[(6,7-dihydro-5H-pyrrolo[1,2-c]imidazol-7-yl) thio]-6-(1-hydroxyethyl)-1-methyl-1-carbapen-2-em-3-carboxylic acid:

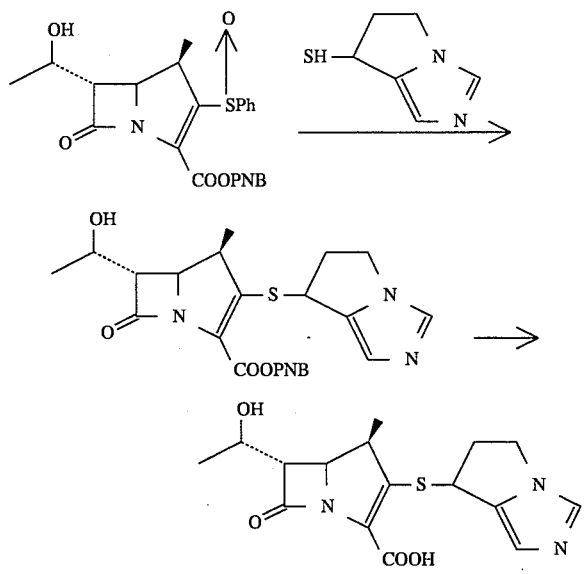

(1) Synthesis of p-nitrobenzyl (1R,5S,6S,8R)-2-[(6,7-dihydro-5H-pyrrolo[1,2-c]imidazol-7-yl)thio]-6-(1-hydroxyethyl)-1-methyl-l-carbapen-2-em-3-carboxylate p-Nitrobenzyl (1R,5S,6S,8R)-6-(1-hydroxyethyl)-1-methyl-2-phenylsulfinyl-1-carbapen-2-em-3-carboxylate (357 mg) was dissolved in a mixture of 2 ml of THF, 2 ml of acetonitrile and 0.5 ml of DMSO, the solution was cooled to −35° C., a solution of 200 mg of 6,7-dihydro-7-mercapto-5H-pyrrolo[1,2-c]imidazole in a mixture of 2 ml of THF and 2 ml of acetonitrile and 1.6 ml of diisopropylethylamine were added thereto with stirring, and the resulting mixture was stirred at that temperature for 120 minutes. Hexane was added to the reaction mixture, the supernatant was removed by decantation and the residue was washed with ether and purified by column chromatography using 5 g of silica gel. The title compound (150 mg ) was obtained from a chloroform-methanol (97:3, v/v) eluate fraction. NMR δ (CDCl$_3$): 1.20–1.44 (6H, m), 2.60–3.40 (4H, m), 3.90–4.50 (4H, m), 4.70–4.90 (1H, m), 5.20 and 5.52 (each 1H, each d, J=15 Hz), 6.92 (1H, br s), 7.52 (1H, s), 7.68 and 8.24 (each 2H, each D, J=9 Hz)

(2) Synthesis of (1R,5S,6S,8R)-2-[(6,7-dihydro-5H-pyrrolo[1,2-c]imidazol-7-yl)thio]-6-(1-hydroxyethyl)-1-methyl-1-carbapen-2-em-3-carboxylic acid To a solution of 230 mg of the compound obtained in the above-mentioned step (1) in a mixture of 20 ml of THF and 20 ml of water were added 28 mg of sodium bicarbonate and 200 mg of 10% Pd-C, and catalytic reduction was carried out in a hydrogen stream at a pressure of 4 atmos for 15 minutes. The catalyst was filtered off, the filtrate and washing were combined and concentrated under reduced pressure, and the concentrate was purified by column chromatography using Diaion® HP-20 (Mitsubishi Corp.; 20×300 mm). The initial 100-ml fraction obtained by elution with water was discarded. Elution was continued with water and then with 5% (v/v) THF-water, the eluate fractions were combined and concentrated under reduced pressure, and the concentrate was purified by high-performance liquid chromatography (HPLC) [carrier: Nucleosil® 7C$_{18}$ (10×300 mm); solvent: 3% (v/v) acetonitrile-water; flow rate: 5 ml/min]. The product-containing fractions corresponding to retention times of 12.1 minutes and 13.4 minutes, respectively, were collected and lyophilized to give light-yellow powdery isomers A and B, respectively. (Yields: 14 mg of isomer A and 13 mg of isomer B ).

Isomer A:

UV λ$_{max}$ (H$_2$O): 300 nm

NMR δ (D$_2$O): 1.295 (3H, d, J=7.2 Hz), 1.32 (3H, d, J=6.4 Hz), 2.62–2.66 (1H, m), 3.11–3.16 (1H, m), 3.43–3.50 (2H, m), 4.17–4.29 (4H, m), 4.80 (HOD), 4.83–4.85 (1H, m), 6.93 (1H, br s), 7.73 (1H, s)

Retention time in HPLC: 12.1 minutes
[HPLC conditions: as described above]

Isomer B:

UV λ$_{max}$ (H$_2$O): 300 nm

NMR δ (D$_2$O): 1,185 (3H, d, J=7.2 Hz), 1.325 (3H, d, J=6.4 Hz), 2.57–2.61 (1H, m), 3.13–3.17 (1H, m), 3.41–3.48 (2H, m), 4.18–4.31 (4H, m), 4.80 (HOD), 6.86 (1H, br s), 7.71 (1H, s)

Retention time in HPLC: 13.4 minutes
[HPLC conditions: as described above]

EXAMPLE 2

Production of (1R,5S,6S,8R)-2-[(6,7-dihydro-5H-pyrrolo[1,2-c]imidazol-6-yl)thio]-6-(hydroxyethyl)-1-methyl-1-carbapen-2-em-3-carboxylic acid:

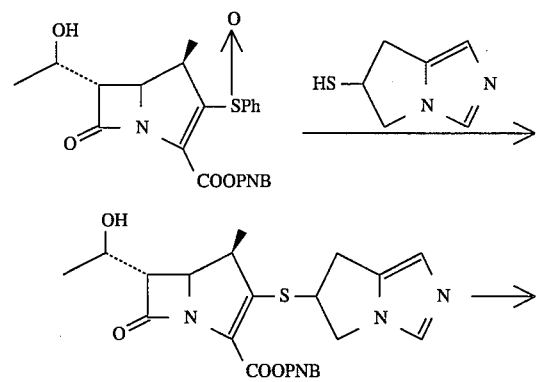

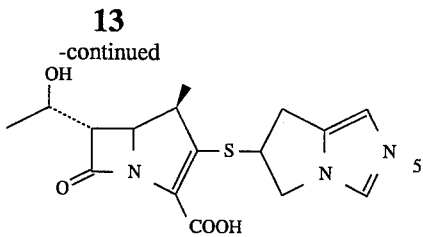

(1) Synthesis of p-nitrobenzyl (1R,5S,6S,8R)-2-[(6,7-dihydro-5H-pyrrolo[1,2-c]imidazol-6-yl)thio]-6-(1-hydroxyethyl)-1-methyl-1-carbapen-2-em-3-carboxylate p-Nitrobenzyl (1R,5S,6S,8R)-6-(1-hydroxyethyl)-1-methyl-2-phenylsulfinyl-1-carbapen-2-em-3-carboxylate (471 mg) was dissolved in a mixture of 3 ml of THF, 3 ml of acetonitrile and 0.5 ml of DMSO, a solution of 762 mg of 6,7-dihydro-6-mercapto-5H-pyrrolo[1,2-c]imidazole in 3 ml of THF and 3 ml of acetonitrile was added thereto with cooling at −50° C. and stirring, and the whole mixture was stirred at −30° C. to −40° C. for 4 hours. Petroleum ether was added to the reaction mixture, the supernatant was removed by decantation, and the residue was washed with isopropyl ether and ether, and subjected to column chromatography using 10 g of silica gel. The title compound was recovered from a chloroform-methanol (92:8, v/v) eluate fraction.

NMR (CDCl$_3$): 1.20–1.4 (6H, m), 2.7–4.6 (9H, m), 5.27 and 5.56 (each 1H, each d, J=15 Hz), 6.7–6.9 (1H, br s), 7.5–7.6 (1H, br s), 7.86 and 8.43 (each 2H, each d, J=9 Hz)

(2) Synthesis of (1R,5S,6S,8R)-2-[(6,7-dihydro-5H-pyrrolo[1,2-c]imidazol-6-yl)thio]-6-(1-hydroxyethyl)-1-methyl-1-carbapen-2-em-3-carboxylic acid:

A 350-mg portion of the compound obtained in the above step (1) was dissolved in a mixture of 15 ml of THF and 15 ml of water, 70 mg of sodium bicarbonate and 250 mg of 10% Pd-C were added thereto, and catalytic reduction was conducted in a hydrogen atmosphere at a pressure of 3.4 atmos for 10 minutes. The catalyst was filtered off, the filtrate and washings were combined and concentrated under reduced pressure, and the concentrate was purified by column chromatography on Diaion® HP-20 (20×300 mm). The initial 100-ml water eluate fraction was discarded, the succeeding water and 5% (v/v) THF-water eluate fraction were combined, concentrated under reduced pressure and subjected to high-performance liquid chromatography (HPLC) [carrier: Nucleosil® 7C$_{18}$ (10×300 mm); solvent: 12% (v/v) methanol-water; flow rate: 6 ml/min ]. Product-containing fractions corresponding to retention times of 7 minutes and 9 minutes were respectively collected and lyophilized to give light-yellow isomers A and B, respectively. (Yields: isomer A: 22 mg; isomer B: 29 mg)

Isomer A:

UV λ$_{max}$ (H$_2$O): 300 nm

NMR δ (D$_2$O): 1.27 (3H, d, J=7.2 Hz), 1.33 (3H, d, J=6.4 Hz), 3.13 (1H, dd, J=16.7, 2.4 Hz), 3.45 (1H, dt, J=16.7, 7.1 Hz), 3.50–3.57 (2H, m), 4.25–4.31 (2H, m), 4.35 (1H, dd, J=12.7, 3.2 Hz), 4.60–4.63 (1H, m), 4.72–4.75 (1H, m), 4.80 (HOD), 7.21 (1H, d, J=1.4 Hz), 8.64 (1H, s)

Retention time in RPLC: 7 minutes
[HPLC conditions: as described above]

Isomer B:

UV λ$_{max}$ (R$_2$O): 300 nm

NMR δ (D$_2$O): 1.28 (3H, d, J=7.2 Hz), 1.33 (3H, d, J=6.4 Hz), 3.05 (1H, dd, J=15.9, 4.8 Hz), 3.44 (1H, dt, J=16.7, 7.1 Hz), 3.51–3.58 (2H, m), 4.25–4.34 (2H, m), 4.36 (1H, dd, J=12.7, 3.2 Hz), 4.60–4.65 (1H, m), 4.72 (1H, dd, J=12.7, 6.3 Hz), 4.80 (HOD), 7.23 (1H, s), 8.62 (1H, s)

Retention time in HPLC: 9 minutes
[HPLC conditions: as described above]

EXAMPLE 3

Production of (1R,5S,6S,8R)-2-[(6,7-dihydro-5H-pyrrolo[1,2-a]imidazol-6-yl)thio]-6-(1-hydroxyethyl)-1-methyl-1-carbapen-2-em-3-carboxylic acid:

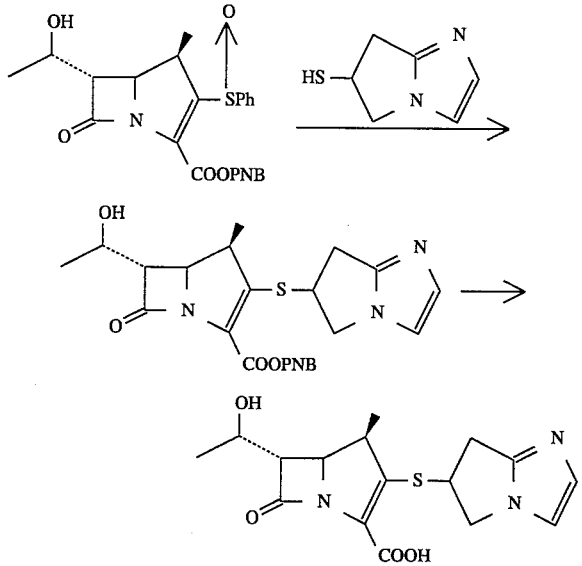

(1) Synthesis of p-nitrobenzyl (1R,5S,6S,8R)-2-[(6,7-dihydro-5H-pyrrolo[1,2-a]imidazol-6-yl)thio]-6-(1-hydroxyethyl)-1-methyl-1-carbapen-2-em-3-carboxylate p-Nitrobenzyl (1R,5S,6S,8R)-6-(1-hydroxyethyl)-1-methyl-2-phenylsulfinyl-1-carbapen-2-em-3-carboxylate (471 mg) was dissolved in a mixture of 5 ml of THF and 0.5 ml of DMSO, the solution was cooled to −50° C., and 280 mg of 6,7-dihydro-6-mercapto-5H-pyrrolo[1,2-a]imidazole and 0.174 ml of diisopropylethylamine were added thereto with stirring. The resulting mixture was stirred at −30° C. to −40° C. for 30 minutes. Petroleum ether was added to the reaction mixture, the supernatant was removed by decantation, and the residue was washed with isopropyl ether and ether, and subjected to column chromatography using 8.5 g of silica gel. The title compound was obtained from a chloroform-methanol (93:7, v/v) eluate fraction. Yield 297 mg.

NMR δ (CDCl$_3$): 1.30 (3H, d, J=6 Hz), 1.38 (3H, d, J=5 Hz), 2.6–3.6 (4H, m), 3.6–4.6 (5H, m), 5.35 (2H, AB q, J=14 Hz), 6.89 (1H, s), 7.05 (1H, s), 7.61 and 8.19 (each 2H, each d, J=9 Hz)

(2) Synthesis of (1R,5S,6S,8R)-2-[(6,7-dihydro-5H-pyrrolo[1,2-a]imidazol-6-yl)thio]-6-(1-hydroxyethyl)-1-methyl-1-carbapen-2-em-3-carboxylic acid The compound obtained in the above step (1) (297 mg) was suspended in a mixture of 7 ml of THF and 12 ml of water, 51 mg of sodium bicarbonate and 120 mg of 10%

Pd-C were added, and catalytic reduction was carried out in a hydrogen atmosphere at a pressure of 4 atmos for 10 minutes. The catalyst was filtered off, the filtrate and washings were combined and concentrated under reduced pressure, and the concentrate was subjected to column chromatography on Daiaion® HP-20 (20×200 mm). The initial 50-ml water eluate fraction was discarded, the succeeding water and 5% (v/v) THF-water eluate fractions were combined, concentrated under reduced pressure and subjected to high-performance liquid chromatography (HPLC) [carrier: Nucleosil® 7C$_{18}$ (20×300 mm); solvent: 5% (v/v) acetonitrile-water; flow rate: 6.5 ml/min] for purification. Product-containing fractions corresponding to retention times of 7 minutes and 8 minutes were respectively collected and lyophilized to give isomers A and B, respectively, each as a light-yellow powder.

(Yields: isomer A: 22 mg, isomer B: 26 mg)

Isomer A:

UV $\lambda_{max}$ (H$_2$O): 297 nm

NMR δ (D$_2$O): 1.29 (3H, d, J=7.2 Hz), 1.33 (3H, d, J=6.4 Hz), 2.92 (1H, dd, J=4.0, 17.5 Hz), 3.35–3.45 (1H, m), 3.45–3.55 (2H, m), 4.12 (1H, dd, J=3.2, 11.1 Hz), 4.25–4.35 (2H, M), 4.50–4.65 (2H, m), 4.80 (HOD), 7.14 (1H, s), 7.17 (1H, s)

Retention time in HPLC: 7 minutes
[HPLC conditions: as described above]

Isomer B:

UV $\lambda_{max}$ (H$_2$)): 299 nm

NMR δ (D$_2$O): 1.27 d, J=7.2 Hz), 1.33 (3H, d, J=6.4 Hz), 3.02 (1H, dd, J=4.0, 17.5 Hz), 3.35–3.45 (1H, m), 3.45–3.55 (2H, m), 4.07 (1H, dd, J=3.2, 11.1 Hz), 4.25–4.35 (2H, m), 4.50–4.65 ( 2H, m), 4.80 (HOD), 7.14 (1H, s), 7.20 (1H, s)

Retention time in HPLC: 8 minutes
[HPLC conditions: as described above]

EXAMPLE 4

Production of (1R,5S,6S,8R)-2-[(6,7-dihydro-5H-pyrrolo[2,1-c ]-1,2,4-triazol-6-yl)thio]-6-(1-hydroxyethyl)-1-methyl-1-carbapen-2-em-3-carboxylic acid:

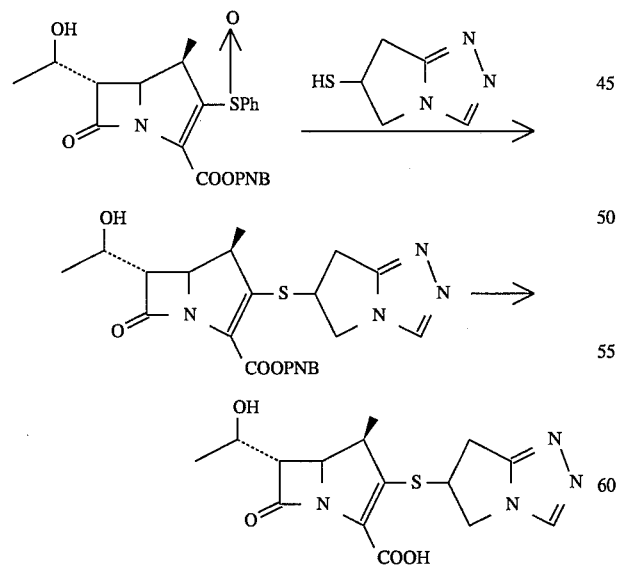

p-Nitrobenzyl (1R,5S,6S,8R)-6-(1-hydroxyethyl)-1-methyl-2-phenylsulfinyl-1-carbapen-2-em-3-carboxylate (471 mg) was dissolved in a mixture of 8 ml of THF, 4 ml of acetonitrile and 4 ml of DMSO, the solution was cooled to −50° C., 545 mg of 6,7-dihydro-6-mercapto-5H-pyrrolo[2,1-c]-1,2,4-triazole trifluoromethanesulfonate and 0.75 ml of diisopropylethylamine were added thereto, and the mixture was stirred at −30° C. to −40° C. for 30 minutes. Ether was added to the reaction mixture, the supernatant was removed by decantation, the residue was washed with isopropyl ether and ether, and then dissolved in a mixture of 5 ml of THF and 5 ml of phosphate buffer (pH 7), 350 mg of 10% Pd-C was added, and catalytic reduction was conducted in a hydrogen atmosphere at a pressure of 4 atmos for 15 minutes.

The catalyst was filtered off, the filtrate and washing were combined and concentrated under reduced pressure, and the concentrate was subjected to column chromatography on Diaion® HP-20 (20×200 nun). The initial 50-ml water eluate fraction was discarded, and the succeeding water and 5% (v/v) THF-water eluate fractions were combined, concentrated under reduced pressure and subjected to high-performance liquid chromatography (HPLC) [carrier: Nucleosil® 7C$_{18}$ (20×300 mm); solvent: 10% (v/v) acetonitrile-water; flow rate: 12 ml/min] for purification. Product-containing fractions corresponding to retention times of 7 minutes and 8 minutes were respectively collected and lyophilized to give isomers A and B, respectively, each as a light-yellow powder.

(Yields: isomer A: 26 mg; isomer B: 9 mg)

Isomer A:

UV $\lambda_{max}$ (H$_2$O): 298 nm

NMR δ (D$_2$O): 1.25 (3H, d, J=7.2 Hz), 1.33 (3H, d, J=6.4 Hz), 2.94 (1H, dd, J=4.0, 17.3 Hz), 3.38–3.45 (2H, m), 3.49 (1H, dd, J=2.4, 5.6 Hz), 3.84 (1H, dd, J=4.8, 11.9 Hz), 4.26–4.30 (2H, m), 4.34 (1H, dd, J=8.0, 11.9 Hz), 4.61–4.64 (1H, m), 4.80 (HOD)

Retention time in HPLC: 8 minutes
[HPLC conditions: as described above]

Isomer B:

UV $\lambda_{max}$ (H$_2$O): 298 nm

NMR δ (D$_2$O): 1.27 (3H, d, J=7.2 Hz), 1.33 (3H, d, J=6.4 Hz), 2.86 (1H, dd, J=4.7, 16.7 Hz), 3.38–3.43 (2H, m), 3.51 (1H, dd, J=2.4, 6.3 Hz), 3.86 (1H, dd, J=4.0, 11.1 Hz), 4.27–4.34 (3H, m), 4.58–4.65 (1H, m), 4.80 (HOD)

Retention time in JPLC: 11 minutes
[HPLC conditions: as described above]

The carbapenem derivatives according to the invention have good physico-chemical stability and potent antimicrobial activity against a wide range of aerobic bacteria, inclusive of gram-positive bacteria, such as *Staphylococcus aureus* S. Smith, *Staphylococcus epidermidis* 56500, *Streptococcus pyrogenes* G-36, *Streptococcus mitis* IID 685, *Streptococcus faecalis* ATCC 19433, etc., and gram-negative bacteria, such as *Escherichia coli* NIHJ, *Shigella flexneri* 2a 5503, *Salmonella enteritidis* IID 604, *Hafnia alvei* IID 978, *Citrobacter freundii* IID 976, *Proteus vulgaris* 08601, *Proteus mirabilis* IFO 3849, *Klebsiella pneumoniae* Type 1, *Enterobacter cloacae* 03402, *Enterobacter aerogenes* ATCC 8329, *Serratia marcescens* 10100, *Yersinia enterocolitica* Te 591, *Alcaligenes faecalis* ATCC 19108, *Pseudomonas aeruginosa* 32233, etc., and further against obligate anaerobes, such as *Bacteroides fragilis* PA-2-11, *Fusobacterium nucleatum* IPP 143, *Clostridium perfringens* 22, *Clostridium difficile* GAI-0547, etc. They are thus useful antimicrobial agents and can be used as drugs for humans and domestic animals, and also for fish.

The compounds according to the invention are usable also as feed preservatives or as disinfectants for medical devices and appliances and so on.

Antibacterial activity data for some of the compounds obtainable in accordance with the invention are shown below. Data for MK-0787 are also shown for comparison.

| Minimum Inhibitory Concentration (MIC, μg/ml) | | | |
|---|---|---|---|
| Test Organism | Compound 1 | Compound 2 | MK-0787 |
| E. coli NIHJ | <0.10 | <0.10 | 0.20 |
| Ent. cloacae 03400 | <0.10 | <0.10 | 0.78 |
| Ser. marcescens 10104 | <0.10 | <0.10 | 1.56 |
| Ps. aeruginosa 32233 | 6.25 | 6.25 | 1.56 |
| S. aureus 209P | <0.10 | <0.10 | <0.10 |
| C. difficile GAI-0747 | 3.13 | 1.56 | 50.0 |

Notes:
Compound 1: Product of Example 2 (isomer B)
Compound 2: Product of Example 3 (isomer B)

While the invention has been described in detail and with reference to specific embodiments thereof, it will be apparent to one skilled in the art that various changes and modifications can be made therein without departing from the spirit and scope thereof.

What is claimed is:

1. A compound of formula (I):

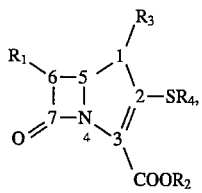

any isomeric form thereof or pharmacologically acceptable salts of the compound of formula (I) or isomeric forms thereof, wherein:

(a) $R_1$ is a hydrogen atom, an alkyl group of from 1 to 6 carbon atoms, a hydroxy-lower alkyl group or a protected hydroxylower alkyl group of from 1 to 6 carbon atoms in its alkyl moiety;

(b) $COOR_2$ is a carboxyl group, a carboxylate anion or a protected carboxyl group;

(c) $R_3$ is an alkyl group of from 1 to 6 carbon atoms; and (d) $R_4$ is selected from the group consisting of

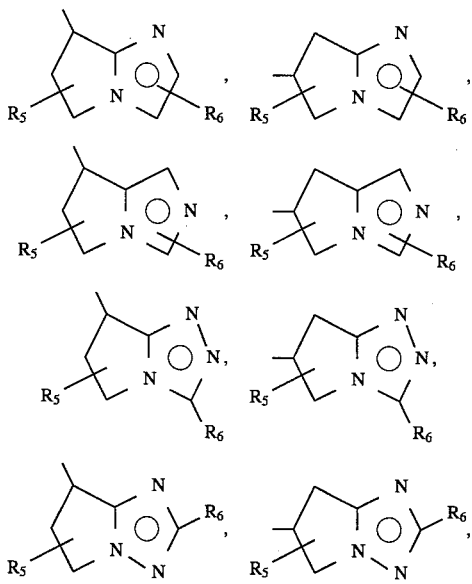

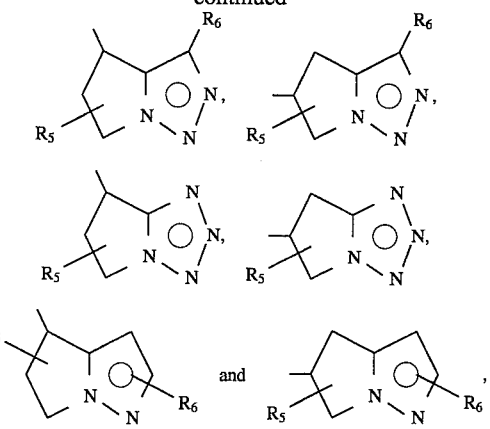

in which $R_6$ is bound to a carbon atom and wherein $R_5$ and $R_6$ are the same or different and each is selected from the group consisting of a hydrogen atom, a halogen atom, a hydroxyl group, a carbamate group, an alkoxyl group of from 1 to 6 carbon atoms, an amino group, an acylamino group, a ureido group, an alkylthio group of from 1 to 6 carbon atoms, a sulfenyl group, a sulfinyl group, a sulfonamido group, a carbamoyl group, a cyano group, a nitro group, an amidino group, a quanidino group, a hydroxycarbamoyl group, a thiocarbamoyl group, a trifluoromethyl group, an imino group, a $C_1$–$C_6$ alkyl group which may be substituted, a $C_2$–$C_6$ alkenyl group which may be substituted, a $C_2$–$C_6$ alkynyl group which may be substituted, a $C_3$–$C_6$ cycloalkyl group which may be substituted, a $C_3$–$C_6$ cycloalkenyl group which may be substituted, a heterocyclyl group which may be substituted, a heterocyclyl-$C_1$–$C_6$ alkyl group which may be substituted, a heterocyclyl-$C_2$–$C_6$ alkenyl group which may be substitute, a heterocyclyl-$C_2$–$C_6$ alkynyl group which may be substituted, a $C_3$–$C_6$ cycloalkylidene group which may be substituted, and a $C_3$–$C_6$ heterocycloalkylidene group which may be substituted, wherein the heterocyclyl group, heterocyclyl-$C_1$–$C_6$ alkyl group, heterocyclo-$C_2$–$C_6$ heterocycloalkylidene is a substituent selected from the group consisting of piperizino, 4-piperizinyl, piperazino and morpholino, and the substituent or substituents on the group $R_5$ or $R_6$ being selected each independently from the group consisting of a halogen atom, a hydroxyl group, an alkoxy group of from 1 to 6 carbon atoms, a carbamoyloxy group which may have one or two substituents selected from the group consisting of a $C_1$–$C_6$ alkyl group, an amino group which may have one or two substituents selected from the group consisting of a $C_1$–$C_6$ alkyl group, an alkylammonio group which may have up to three $C_1$–$C_6$ alkyl groups, an acylamino group which may have a substituent selected from the group consisting of a $C_1$–$C_6$ alkyl group, a formylamino group, a ureido group which may have 1 to 4 substituents selected from the group consisting of a $C_1$–$C_6$ alkyl group, an alkylthio group, a sulfenyl group, a sulfinyl group, a sulfamoyl group which may have one or two substituents selected from the group consisting of a $C_1$–$C_6$ alkyl group, a sulfinamoyl group which may have one or two substituents selected from the group consisting of a $C_1$–$C_6$ alkyl group, a carbamoyl group which may have one or two substituents selected from the group consisting of a $C_1$–$C_6$ alkyl group, a cyano group, a nitro group, a amidino group which may have one or two substituents selected from the group consisting of a $C_1$–$C_6$ alkyl group, a guanidino group which may have one or two substituents selected from the group consisting of a $C_1$–$C_6$ alkyl group, a hydroxycarbamoyl group which may have a substituent selected from the group consisting of a $C_1C_6$ alkyl group, a thiocarbamoyl group which may have one or two substituents selected from the group consisting of a $C_1$–$C_6$ alkyl group, a trifluoromethyl group, an alkoxyimino group, a $C_1$–$C_6$ alkoxycarbonyl group which may be substituted and a $C_1$–$C_6$ alkoxycarbonyloxy group which may be substituted.

2. A compound as claimed in claim 1, wherein the substituent $R_1$ is a 1-hydroxyethyl group.

3. A compound as claimed in claim 2, said compound being a (1R, 5S, 6S, 8S)-6-(1-hydroxyethyl)-1-methylcarbapenem derivative.

4. A compound as claimed in claim 1, said compound being represented by formula (Ia):

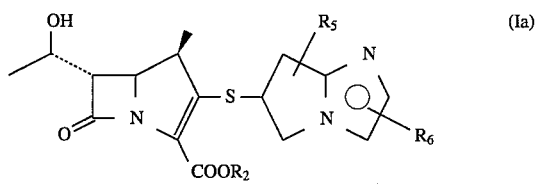

wherein $R_2$ is a hydrogen atom, or $COOR_2$ is a carboxylate anion and $R_5$ and $R_6$ are the same or different and each is a hydrogen atom, —$CH_3$, —$CH_2OH$, —$CONH_2$, —$CONHCH_3$ or —$CON(CH_3)_2$.

5. A compound as claimed in claim 1, said compound being represented by the formula (Ib):

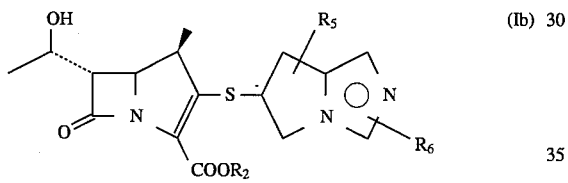

wherein $R_2$ is a hydrogen atom, or $COOR_2$ is a carboxylate anion and $R_5$ and $R_6$ are the same or different and each is a hydrogen atom, —$CH_3$, —$CH_2OH$, —$CONH_2$, —$CONHCH_3$ or —$CON(CH_3)_2$.

6. A compound as claimed in claim 1, said compound being represented by the formula (Ic):

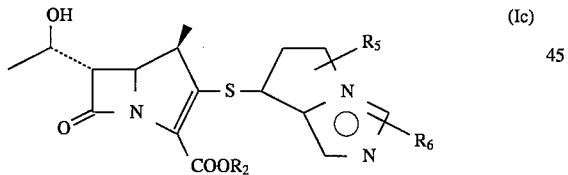

wherein $R_2$ is a hydrogen atom, or $COOR_2$ is a carboxylate anion and $R_5$ and $R_6$ are the same or different and each is a hydrogen atom, —$CH_3$, —$CH_2OH$, —$CONH_2$, —$CONHCH_3$ or —$CON(CH_3)_2$.

7. A compound as claimed in claim 1, said compound being represented by the formula (Id):

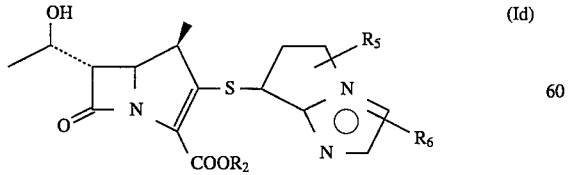

wherein $R_2$ is hydrogen atom, or $COOR_2$ is a carboxylate anion and $R_5$ and $R_6$ are the same or different and each is a hydrogen atom, —$CH_3$, —$CH_2OH$, —$CONH_2$, —$CONHCH_3$ or —$CON(CH_3)_2$.

8. A compound as claimed in claim 1, said compound being represented by the formula (Ie):

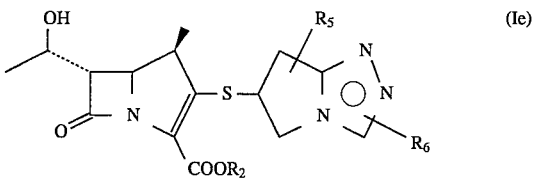

wherein $R_2$ is hydrogen atom, or $COOR_2$ is a carboxylate anion and $R_5$ and $R_6$ are the same or different and each is a hydrogen atom, —$CH_3$, —$CH_2OH$, —$CONH_2$, —$CONHCH_3$ or —$CON(CH_3)_2$.

9. A compound as claimed in claim 1, said compound being represented by the formula (If):

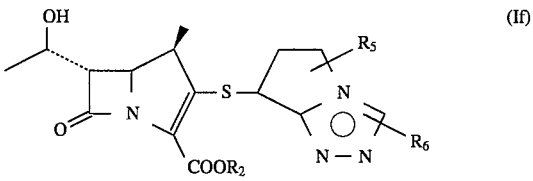

wherein $R_2$ is a hydrogen atom, or $COOR_2$ is a carboxylate anion and $R_5$ and $R_6$ are the same or different and each is a hydrogen atom, —$CH_3$, —$CH_2OH$, —$CONH_2$, —$CONHCH_3$ or —$CON(CH_3)_2$.

10. A compound of formula (I):

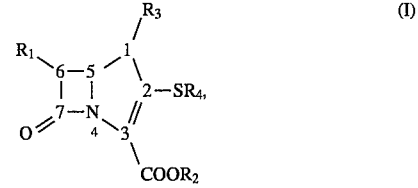

any isomeric form thereof or pharmacologically acceptable salts of the compound of formula (I) or isomeric forms thereof, wherein:

(a) $R_1$ is a hydrogen atom, an alkyl group of from 1 to 6 carbon atoms, a hydroxy-lower alkyl group or a protected hydroxy-lower alkyl group of from 1 to 6 carbon atoms in its alkyl moiety;

(b) $R_2$ is a hydrogen atom, a stratight or branched $C_1$–$C_4$ alkyl group, a $C_1$–$C_6$ alkoxy-$C_1$–$C_6$ alkyl group, $C_1$–$C_6$ aliphatic acyloxymethyl group or a phthalidyl group;

(c) $R_3$ is an alkyl group of from 1 to 6 carbon atoms; and (d) $R_4$ is selected from the group consisting of

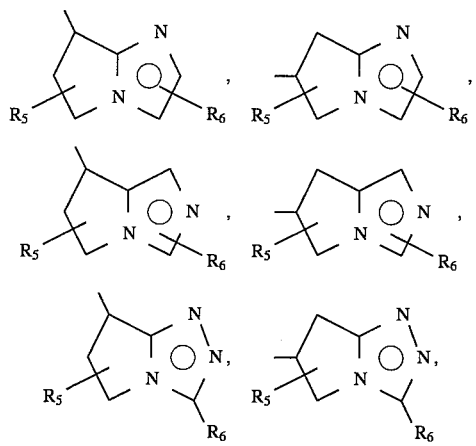

-continued

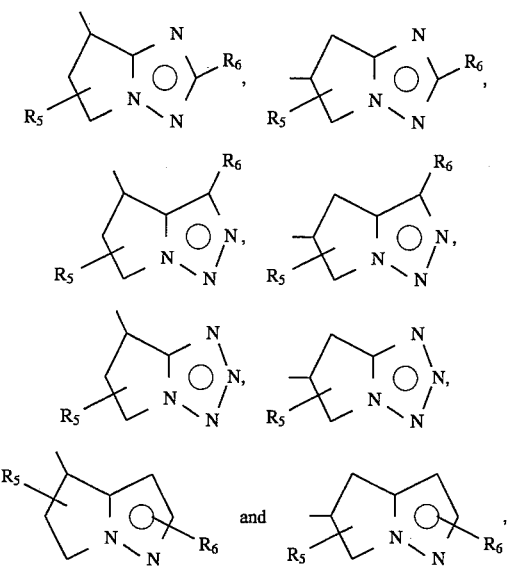

in which $R_6$ is bound to a carbon atom and wherein $R_5$ and $R_6$ are the same or different and each is selected from the group consisting of a hydrogen atom, a halogen atom, a hydroxyl group, a carbamate group, an alkoxyl group of from 1 to 6 carbon atoms, an amino group, an acylamino group, a ureido group, an alkylthio group of from 1 to 6 carbon atoms, a sulfenyl group, a sulfinyl group, a sulfonamido group, a carbamoyl group, a cyano group, a nitro group, an amidino group, a quanidino group, a hydroxycarbamoyl group, a thiocarbamoyl group, a trifluoromethyl group, an imino group, a $C_1$–$C_6$ alkyl group which may be substituted, a $C_2$–$C_6$ alkenyl group which may be substituted, a $C_2$–$C_6$ alkynyl group which may be substituted, a $C_3$–$C_6$ cycloalkyl group which may be substituted, a $C_3$–$C_6$ cycloalkenyl group which may be substituted, a heterocyclyl group which may be substituted, a heterocyclyl-$C_1$–$C_6$ alkyl group which may be substituted, a heterocyclyl-$C_2$–$C_6$ alkenyl group which may be substituted, a heterocyclyl-$C_2$–$C_6$ alkynyl group which may be substituted, a $C_3$–$C_6$ cycloalkylidene group which may be substituted, and a $C_3$–$C_6$ heterocycloalkylidene group which may be substituted, wherein the heterocyclyl group, heterocyclyl-$C_1$–$C_6$ alkyl group, heterocyclo-$C_2$–$C_6$ heterocycloalkylidene is a substituent selected from the group consisting of piperizino, 4-piperizinyl, piperazino and morpholino, and the substituent or substituents on the group $R_5$ or $R_6$ being selected each independently from the group consisting of a halogen atom, a hydroxyl group, an alkoxy group of from 1 to 6 carbon atoms, a carbamoyloxy group which may have one or two substituents selected from the group consisting of a $C_1$–$C_6$ alkyl group, an amino group which may have one or two substituents selected from the group consisting of a $C_1$–$C_6$ alkyl group, an alkylammonio group which may have up to three $C_1$–$C_6$ alkyl groups, an acylamino group which may have a substituent selected from the group consisting of a $C_1$–$C_6$ alkyl group, a formylamino group, a ureido group which may have 1 to 4 substituents selected from the group consisting of a $C_1$–$C_6$ alkyl group, an alkylthio group, a sulfenyl group, a sulfinyl group, a sulfamoyl group which may have one or two substituents selected from the group consisting of a $C_1$–$C_6$ alkyl group, a sulfinamoyl group which may have one or two substituents selected from the group consisting of a $C_1$–$C_6$ alkyl group, a carbamoyl group which may have one or two substituents selected from the group consisting of a $C_1$–$C_6$ alkyl group, a cyano group, a nitro group, a amidino group which may have one or two substituents selected from the group consisting of a $C_1$–$C_6$ alkyl group, a guanidino group which may have one or two substituents selected from the group consisting of a $C_1$–$C_6$ alkyl group, a hydroxycarbamoyl group which may have a substituent selected from the group consisting of a $C_1$–$C_6$ alkyl group, a thiocarbamoyl group which may have one or two substituents selected from the group consisting of a $C_1$–$C_6$ alkyl group, a trifluoromethyl group, an alkoxyimino group, a $C_1$–$C_6$ alkoxycarbonyl group which may be substituted and a $C_1$–$C_6$ alkoxycarbonyloxy group which may be substituted.

11. A compound as claimed in claim 10, wherein the C–$C_6$ aliphatic acyloxymethyl group is a pivaloyloxymethyl group.

12. A compound as claimed in claim 10, said compound being represented by formula (Ig):

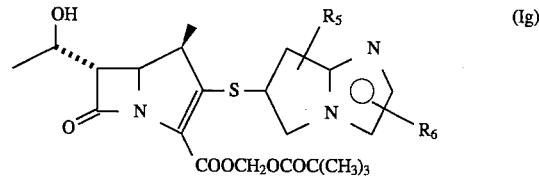

wherein $R_5$ and $R_6$ are the same or different and each is a hydrogen atom, —$CH_3$, —$CH_2OH$, —$CONH_2$, —CONHCH_3$ or —$CON(CH_3)_2$.

13. A compound as claimed in claim 10, said compound being represented by formula (Ih):

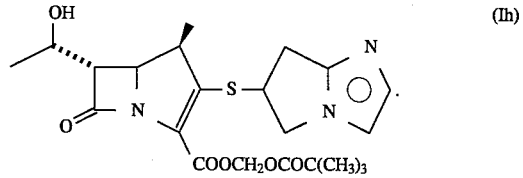

* * * * *